(12) United States Patent
Slayton et al.

(10) Patent No.: US 10,245,449 B2
(45) Date of Patent: *Apr. 2, 2019

(54) SYSTEMS AND METHODS FOR COUPLING AN ULTRASOUND SOURCE TO TISSUE

(71) Applicant: Guided Therapy Systems, LLC, Mesa, AZ (US)

(72) Inventors: Michael H. Slayton, Tempe, AZ (US); Peter G. Barthe, Phoenix, AZ (US); Paul Jaeger, Mesa, AZ (US)

(73) Assignee: Guided Therapy Systems, LLC, Mesa, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/293,361

(22) Filed: Oct. 14, 2016

(65) Prior Publication Data

US 2017/0028226 A1 Feb. 2, 2017

Related U.S. Application Data

(60) Division of application No. 13/547,023, filed on Jul. 11, 2012, now Pat. No. 9,504,446, which is a continuation-in-part of application No. 13/136,544, filed on Aug. 2, 2011, now Pat. No. 9,149,658.

(60) Provisional application No. 61/506,609, filed on Jul. 11, 2011, provisional application No. 61/506,610, filed on Jul. 11, 2011, provisional application No. 61/369,782, filed on Aug. 2, 2010, provisional application No. 61/369,793, filed on Aug. 2, 2010, (Continued)

(51) Int. Cl.
*A61N 7/02* (2006.01)
*A61B 8/00* (2006.01)
*A61B 18/00* (2006.01)
*A61N 7/00* (2006.01)
*A61B 90/00* (2016.01)

(52) U.S. Cl.
CPC ............... *A61N 7/02* (2013.01); *A61B 8/429* (2013.01); *A61B 8/56* (2013.01); *A61B 2018/00642* (2013.01); *A61B 2018/00898* (2013.01); *A61B 2090/378* (2016.02); *A61N 2007/006* (2013.01); *A61N 2007/0034* (2013.01); *A61N 2007/0091* (2013.01); *A61N 2007/0095* (2013.01); *A61N 2007/027* (2013.01)

(58) Field of Classification Search
CPC ...................... A61B 8/429; A61B 2018/00642
See application file for complete search history.

(56) References Cited

U.S. PATENT DOCUMENTS 4,736,130 A * 4/1988 Puskas ................. B06B 1/0215
310/316.01
5,406,503 A * 4/1995 Williams, Jr. ...... A61F 9/00745
604/22

(Continued)

*Primary Examiner* — Angela M Hoffa
(74) *Attorney, Agent, or Firm* — Quarles & Brady LLP

(57) ABSTRACT

This disclosure provides systems and methods for sensing coupling of an ultrasound source to a target and for providing a constant average output of power from an ultrasound source. The systems and methods can include a frequency sweep function. The systems and methods can also include receiving reflected energy from an acoustic window and determining a feedback using the reflected energy. The systems and methods can also include comparing the feedback with a threshold level and using the comparison to determine if the ultrasound source is coupled with a target.

1 Claim, 6 Drawing Sheets

Related U.S. Application Data provisional application No. 61/369,806, filed on Aug. 2, 2010, provisional application No. 61/370,095, filed on Aug. 2, 2010.

(56) References Cited

U.S. PATENT DOCUMENTS

| | | | | |
|---|---|---|---|---|
| 5,735,280 A | * | 4/1998 | Sherman | A61B 17/2202 600/1 |
| 6,273,884 B1 | * | 8/2001 | Altshuler | A61B 18/203 606/2 |
| 6,610,011 B2 | * | 8/2003 | Emery | A61B 5/6843 600/437 |
| 8,831,710 B2 | * | 9/2014 | Kobayashi | A61B 1/00165 600/117 |
| 9,149,658 B2 | * | 10/2015 | Barthe | A61N 7/02 |
| 9,504,446 B2 | * | 11/2016 | Jaeger | A61N 7/02 |
| 2001/0014780 A1 | * | 8/2001 | Martin | A61B 17/22004 601/2 |
| 2004/0082857 A1 | * | 4/2004 | Schonenberger | A61B 8/4438 600/439 |
| 2006/0094988 A1 | * | 5/2006 | Tosaya | A61H 23/0245 601/2 |
| 2006/0229514 A1 | * | 10/2006 | Wiener | A61B 17/32009 600/471 |
| 2007/0060819 A1 | * | 3/2007 | Altshuler | A61B 5/0059 600/475 |
| 2008/0167556 A1 | * | 7/2008 | Thompson | A61N 7/00 600/439 |
| 2008/0281237 A1 | * | 11/2008 | Slayton | A61B 8/4281 601/2 |
| 2012/0029353 A1 | * | 2/2012 | Slayton | A61N 7/02 600/439 |
| 2012/0323095 A1 | * | 12/2012 | Baker, Jr. | A61B 5/14551 600/324 |
| 2012/0330194 A1 | * | 12/2012 | Britva | A61N 7/00 601/2 |
| 2013/0172757 A1 | * | 7/2013 | Frigstad | A61B 8/4494 600/459 |
| 2014/0058264 A1 | * | 2/2014 | Baym | A61B 8/4227 600/447 |

* cited by examiner

SYSTEMS AND METHODS FOR COUPLING AN ULTRASOUND SOURCE TO TISSUE

CROSS-REFERENCE TO RELATED APPLICATIONS

This application is a divisional of U.S. patent application 13/547,023 filed Jul. 11, 2012, which claims benefit of U.S. Provisional Patent Applications 61/506,609 and 61/506,610, both filed Jul. 11, 2011; all of which are incorporated by reference herein.

U.S. patent application 13/547,023 is also a continuation-in-part of and claims benefit of U.S. patent application 13/136,544 filed Aug. 2, 2011, which claims the benefit of U.S. Provisional Patent Applications 61/369,782, 61/369,793, 61/369,806 and 61/370,095, all filed Aug. 2, 2010; all of which are incorporated by reference herein.

BACKGROUND

Coupling of a treatment system to tissue is important for clinical efficiency of the desired treatment. In addition, using a treatment system that is not coupled to tissue may cause safety concerns. Further, if a treatment system is not properly coupled to the tissue may cause stability and performance issues. Various contact sensors have been used to determine if a treatment system is coupled to targeted tissue. However, these contact sensors typically use mechanical methods to determine if a treatment system is coupled to the tissue. Accordingly, new approaches for determining whether a treatment system is coupled to targeted tissue are needed.

SUMMARY

Various embodiments described herein provide methods and systems for monitoring ultrasound energy. Various embodiments provide a method of sensing coupling of an ultrasound source to a target. In some embodiments, the method comprises providing an ultrasound sound source comprising a transducer, an acoustically transparent standoff, an acoustic window at a bottom surface of the standoff, and a frequency sweep function coupled to the transducer. In some embodiments, the method can comprise emitting ultrasound energy from the transducer; receiving reflected energy; frequency sweeping the transducer; determining the feedback from the frequency sweep is above a threshold level; and determining of the source is coupled to the target.

In some embodiments, if the feedback from the frequency is above the threshold level, then the source is not coupled to the target. In some embodiments, if the feedback from the frequency is below the threshold level, then the source is coupled to the target.

Various embodiments provide a system for determining whether an ultrasound source is coupled to a target. In some embodiments, the system comprises an ultrasound source comprising a transducer; an acoustically transparent standoff coupled to the transducer; a half wavelength acoustic window at a bottom surface of the standoff, and a frequency sweep function coupled to the transducer.

Various embodiments provide a system for providing a constant average output of power from an ultrasound source. In some embodiments, the system comprises an ultrasound transducer coupled to a power supply; a controller in communication with the power supply; a chirp function in communication with and operable to monitor the ultrasound transducer; a feedback loop from the chirp function to the controller. In some embodiments, the controller is operable to change a parameter on the transducer based on the feedback to provide a constant average output of power from the ultrasound transducer.

DRAWINGS

The present disclosure will become more fully understood from the description and the accompanying drawings, wherein.

DESCRIPTION

Figure 1:
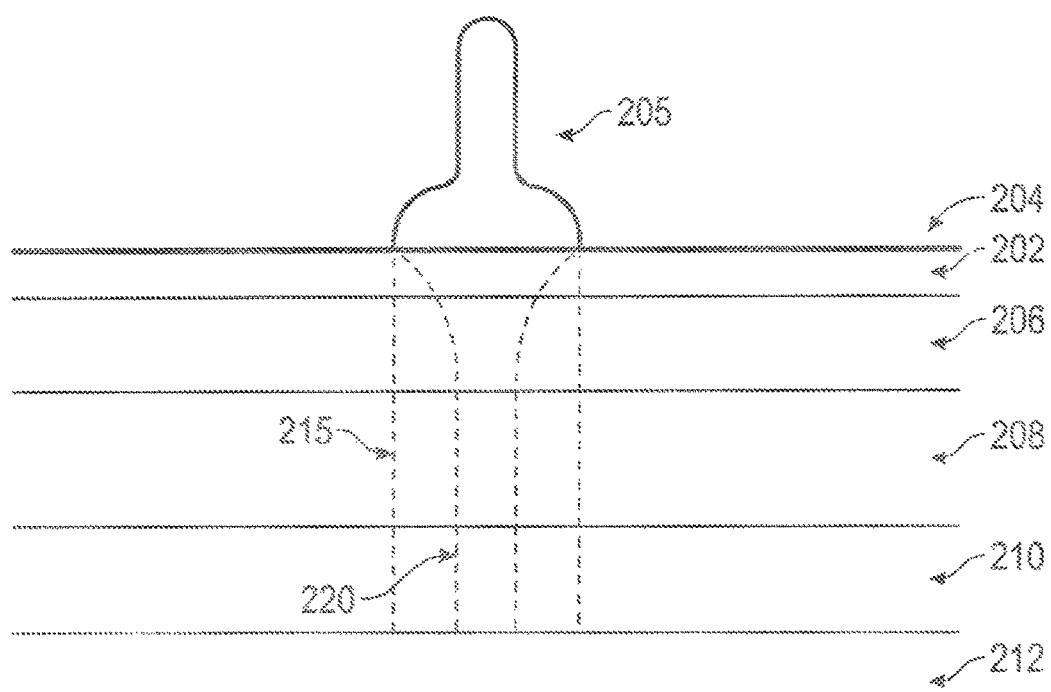
FIG. 1 is a cross sectional view illustrating tissue layers and ultrasound energy directed to a portion of the tissue layers, in accordance with various non-limiting embodiments.

The following description is merely exemplary in nature and is in no way intended to limit the various embodiments, their application, or uses. As used herein, the phrase "at least one of A, B, and C" should be construed to mean a logical (A or B or C), using a non-exclusive logical "or." As used herein, the phrase "A, B and/or C" should be construed to mean (A, B, and C) or alternatively (A or B or C), using a non-exclusive logical "or." It should be understood that steps within a method may be executed in different order without altering the principles of the present disclosure.

The drawings described herein are for illustrative purposes only of selected non-limiting embodiments and not all possible implementations, and are not intended to limit the scope of any of the various embodiments disclosed herein or any equivalents thereof. It is understood that the drawings are not drawn to scale. For purposes of clarity, the same reference numbers will be used in the drawings to identify similar elements.

The various embodiments may be described herein in terms of various functional components and processing steps. It should be appreciated that such components and steps may be realized by any number of hardware components configured to perform the specified functions. For example, various embodiments may employ various medical treatment devices, visual imaging and display devices, input terminals and the like, which may carry out a variety of functions under the control of one or more control systems or other control devices. In addition, the embodiments may be practiced in any number of medical contexts and that the various embodiments relating to a method and system for acoustic energy deposition in tissue, as described herein, are merely indicative of one of the many applications for the invention. For example, the principles, features and methods discussed may be applied to any medical application. Further, various aspects of the various embodiments may be suitably applied to cosmetic applications. Moreover, some of the embodiments may be applied to cosmetic enhancement of skin and/or various soft tissue layers.

Various embodiments provide methods and systems to adjust a temperature of a transducer, in order to maintain maximum efficiency of power applied by the transducer. Some embodiments provide methods and systems to minimize or eliminate temperature saturation of a transducer during the delivery of power to the transducer. In some embodiments, methods and systems can control a temperature of a transducer to maintain a desired frequency of energy transmission at a maximum power.

Various embodiments provide methods and systems to adjust a temperature of a transducer, in order to maintain maximum efficiency of power applied by the transducer. Some embodiments provide methods and systems to minimize or eliminate temperature saturation of a transducer during the delivery of power to the transducer. In some embodiments, methods and systems can control a temperature of a transducer to maintain a desired frequency of energy transmission at a maximum power.

Some embodiments provide a method of providing ultrasound energy having a stable power output. The method can comprise providing ultrasound energy from a ultrasound transducer; determining a power level threshold of the ultrasound energy; monitoring a power level of the ultrasound energy over time of the ultrasound energy; communicating a power level to a controller; adjusting the frequency of the ultrasound energy upon a change in the power level; and maintaining the power level threshold of the ultrasound energy.

In some embodiments, the method can further comprise emitting the ultrasound energy at a specific frequency and correcting the frequency to the specific frequency upon a change in the power level. In some embodiments, the method can comprise changing power provided to a transducer providing the ultrasound energy based on the adjusting the frequency of the ultrasound energy. In some embodiments, the method can comprise terminating the providing the ultrasound energy upon a change of the power level above the power level threshold.

Some embodiments provide a method of providing ultrasound energy having a stable power output. The method can comprise providing ultrasound energy from an ultrasound transducer; determining a power level threshold of the ultrasound energy; monitoring a temperature of the ultrasound transducer over time; communicating the temperature to a controller; adjusting the frequency of the ultrasound energy upon a change in the temperature; and maintaining the power level threshold of the ultrasound energy.

In some embodiments, the method can further comprise determining a temperature threshold of the ultrasound transducer and terminating the providing ultrasound energy when the temperature is above the temperature threshold.

In some embodiments, the method can further comprise emitting the ultrasound energy at a specific frequency and correcting the frequency to the specific frequency upon the change of temperature. In some embodiments, the method can comprise terminating the providing the ultrasound energy upon a change of the power level above the power level threshold. In some embodiments, the method can further comprise determining a temperature threshold of the ultrasound transducer and terminating the providing ultrasound energy when a temperature of the ultrasound transducer is above the temperature threshold.

Some embodiments provide a method of providing ultrasound energy having a stable power output. The method can comprise providing ultrasound energy from an ultrasound transducer; determining a voltage threshold of the ultrasound energy; monitoring a voltage of the ultrasound transducer over time; communicating the voltage to a controller; adjusting the frequency of the ultrasound energy upon a change in the voltage; and maintaining the power level threshold of the ultrasound energy.

In some embodiments, the method can further comprise determining a temperature threshold of the ultrasound transducer and terminating the providing ultrasound energy when the temperature of the ultrasound transducer is above the temperature threshold.

In some embodiments, the method can further comprise emitting the ultrasound energy at a specific frequency and correcting the frequency to the specific frequency upon the change of voltage. In some embodiments, the method can comprise terminating the providing the ultrasound energy upon a change of the power level above the power level threshold.

Some embodiments provide a method of providing ultrasound energy having a stable power output. The method can comprise providing ultrasound energy from a ultrasound transducer; determining a voltage threshold of the ultrasound energy; monitoring a voltage of the ultrasound transducer over time; communicating the voltage to a controller; adjusting the frequency of the ultrasound energy upon an change in the voltage; monitoring a power level of the ultrasound energy over time of the ultrasound energy; communicating a power level to a controller; adjusting the frequency of the ultrasound energy upon a change in the power level; and maintaining the power level threshold of the ultrasound energy.

In some embodiments, the method can further comprise determining a temperature threshold of the ultrasound transducer and terminating the providing ultrasound energy when the temperature of the ultrasound transducer is above the temperature threshold.

In some embodiments, the method can further comprise emitting the ultrasound energy at a specific frequency and correcting the frequency to the specific frequency upon the change of voltage. In some embodiments, the method can comprise terminating the providing the ultrasound energy upon a change of the power level above the power level threshold.

Some embodiments provide a method of providing ultrasound energy having a stable power output. The method can comprise providing ultrasound energy from a ultrasound transducer; monitoring a power level of the ultrasound energy over time of the ultrasound energy; communicating a power level to a controller; adjusting the frequency of the ultrasound energy upon a change in the power level; monitoring a temperature of the ultrasound transducer over time; communicating the temperature to a controller; adjusting the frequency of the ultrasound energy upon an change in the temperature; and maintaining the power level threshold of the ultrasound energy.

In some embodiments, the method can further comprise determining a temperature threshold of the ultrasound transducer and terminating the providing ultrasound energy when the temperature of the ultrasound transducer is above the temperature threshold.

In some embodiments, the method can further comprise emitting the ultrasound energy at a specific frequency and correcting the frequency to the specific frequency upon the change of voltage. In some embodiments, the method can comprise terminating the providing the ultrasound energy upon a change of the power level above the power level threshold.

Some embodiments provide a method of providing ultrasound energy having a stable power output. The method can comprise providing ultrasound energy from a ultrasound transducer; determining a voltage threshold of the ultrasound energy; monitoring a voltage of the ultrasound transducer over time; communicating the voltage to a controller; adjusting the frequency of the ultrasound energy upon an change in the voltage; monitoring a power level of the ultrasound energy over time of the ultrasound energy; communicating a power level to a controller; adjusting the frequency of the ultrasound energy upon a change in the power level; monitoring a temperature of the ultrasound transducer over time; communicating the temperature to a controller; adjusting the frequency of the ultrasound energy upon an change in the temperature; and maintaining the power level threshold of the ultrasound energy.

In some embodiments, the method can further comprise determining a temperature threshold of the ultrasound transducer and terminating the providing ultrasound energy when the temperature of the ultrasound transducer is above the temperature threshold.

In some embodiments, the method can further comprise emitting the ultrasound energy at a specific frequency and correcting the frequency to the specific frequency upon the change of voltage. In some embodiments, the method can comprise terminating the providing the ultrasound energy upon a change of the power level above the power level threshold.

In some embodiments, temperature can be monitored by monitoring changes in time of flight of the ultrasound energy from the transducer. In some embodiments, temperature can be monitored by a piezoelectric sensor that may be a portion of transducer, as described herein. In various embodiments, a controller may use a look up table to change a parameter. In some embodiments, controller can employ hardware, software, or a combination of both to change a parameter such as power, voltage or current.

With reference to FIG. 1, a cross sectional view of tissue layers and ultrasound energy directed to at least one of the tissue layers, according to various embodiments of the present invention, is illustrated. The tissue layers illustrated are skin surface 204, epidermal layer 202, dermis layer 206, fat layer 208, SMAS layer 210, and muscle and connective tissue layer 212. Ultrasound probe 205 transmits ultrasound energy 220 transmitting in ROI 215. In various embodiments, ultrasound probe 205 is capable of transmitting ultrasound energy 220 transmitting at variable depths in ROI 215, such as, for example, the depths described herein. Ultrasound probe 205 is capable of transmitting therapeutic ultrasound energy as a single frequency, variable frequencies, or a plurality of frequencies, such as, for example, within the frequency ranges described herein. Ultrasound probe 205 is capable of transmitting ultrasound energy 220 transmitting for variable time periods or to pulse the transmission over time, such as, for example, those time intervals described herein. Ultrasound probe 205 is capable of providing various energy levels of therapeutic ultrasound energy, such as, for example, the energy levels described herein.

Ultrasound probe 205 may be individual hand-held device, or may be part of a treatment system or part of cosmetic enhancement system. The ultrasound probe 205 can provide both therapeutic ultrasound energy and imaging ultrasound energy. However, ultrasound probe 205 may provide only therapeutic ultrasound energy. Ultrasound probe 205 may comprise a therapeutic transducer and a separate imaging transducer. Ultrasound probe 205 may comprise a transducer or a transducer array capable of both therapeutic and imaging applications. According an alternative embodiment, ultrasound probe 205 is coupled directly to one of the tissue layers, as opposed to skin surface 204 to treat the tissue layer. For example, ultrasound probe 205 can be integrated to or attached to a tool, such as, for example, an arthroscopic tool, laparoscopic tool, or an endoscopic tool that may be inserted into a patient's body with minimal invasiveness.

In various embodiments, the ultrasound energy level is in a range of about 0.1 joules to about 500 joules in order to create an ablative lesion. However, the ultrasound energy 108 level can be in a range of from about 0.1 joules to about 100 joules, or from about 1 joules to about 50 joules, or from about 0.1 joules to about 10 joules, or from about 50 joules to about 100 joules, or from about 100 joules to about 500 joules, or from about 50 joules to about 250 joules.

Further, the amount of time ultrasound energy is applied at these levels varies in the range from approximately 1 millisecond to several minutes. However, a range can be from about 1 millisecond to about 5 minutes, or from about 1 millisecond to about 1 minute, or from about 1 millisecond to about 30 seconds, or from about 1 millisecond to about 10 seconds, or from about 1 millisecond to about 1 second, or from about 1 millisecond to about 0.1 seconds, or about 0.1 seconds to about 10 seconds, or about 0.1 seconds to about 1 second, or from about 1 millisecond to about 200 milliseconds, or from about 1 millisecond to about 0.5 seconds.

The frequency of the ultrasound energy can be in a range from about 0.1 MHz to about 100 MHz, or from about 0.1 MHz to about 50 MHz, or from about 1 MHz to about 50 MHz or about 0.1 MHz to about 30 MHz, or from about 10 MHz to about 30 MHz, or from about 0.1 MHz to about 20 MHz, or from about 1 MHz to about 20 MHz, or from about 20 MHz to about 30 MHz.

The frequency of the ultrasound energy can be in a range from about 1 MHz to about 12 MHz, or from about 5 MHz to about 15 MHz, or from about 2 MHz to about 12 MHz or from about 3 MHz to about 7 MHz.

In some embodiments, the ultrasound energy can be transmitted to depths at or below a skin surface in a range from about 0 mm to about 150 mm, or from about 0 mm to about 100 mm, or from about 0 mm to about 50 mm, or from about 0 mm to about 30 mm, or from about 0 mm to about 20 mm, or from about 0 mm to about 10 mm, or from about 0 mm to about 5 mm. In some embodiments, the ultrasound energy can be transmitted to depths below a skin surface in a range from about 5 mm to about 150 mm, or from about 5 mm to about 100 mm, or from about 5 mm to about 50 mm, or from about 5 mm to about 30 mm, or from about 5 mm to about 20 mm, or from about 5 mm to about 10 mm. In some embodiments, the ultrasound energy can be transmitted to depths below a skin surface in a range from about 10 mm to about 150 mm, or from about 10 mm to about 100 mm, or from about 10 mm to about 50 mm, or from about 10 mm to about 30 mm, or from about 10 mm to about 20 mm, or from about 0 mm to about 10 mm.

In some embodiments, the ultrasound energy can be transmitted to depths at or below a skin surface in the range from about 20 mm to about 150 mm, or from about 20 mm to about 100 mm, or from about 20 mm to about 50 mm, or from about 20 mm to about 30 mm. In some embodiments, the ultrasound energy can be transmitted to depths at or below a skin surface in a range from about 30 mm to about 150 mm, or from about 30 mm to about 100 mm, or from about 30 mm to about 50 mm. In some embodiments, the ultrasound energy can be transmitted to depths at or below a skin surface in a range from about 50 mm to about 150 mm, or from about 50 mm to about 100 mm. In some embodiments, the ultrasound energy can be transmitted to depths at or below a skin surface in a range from about 20 mm to about 60 mm, or from about 40 mm to about 80 mm, or from about 10 mm to about 40 mm, or from about 5 mm to about 40 mm, or from about 0 mm to about 40 mm, or from about 10 mm to about 30 mm, or from about 5 mm to about 30 mm, or from about 0 mm to about 30 mm.

In various embodiments, a temperature of tissue receiving the ultrasound energy can be in a range from 30° C. to about 100° C., or from 43° C. to about 60° C., or from 50° C. to about 70° C., or from 30° C. to about 50° C., or from 43° C. to about 100° C., or from 33° C. to about 100° C., or from 30° C. to about 65° C., or from 33° C. to about 70° C., as well as variations thereof.

Also, depending at least in part upon a specific biological effect and the tissue layers that are targeted, temperature of tissue receiving the ultrasound energy within ROI 215 may change in a range from approximately 10° C. to about 15° C. In various embodiments, a temperature of tissue receiving the ultrasound energy is raised to a temperature in a range from about 40° C. to about 55° C., or from about 43° C. to about 48° C., or below a threshold of ablation of the tissue.

Figure 2:
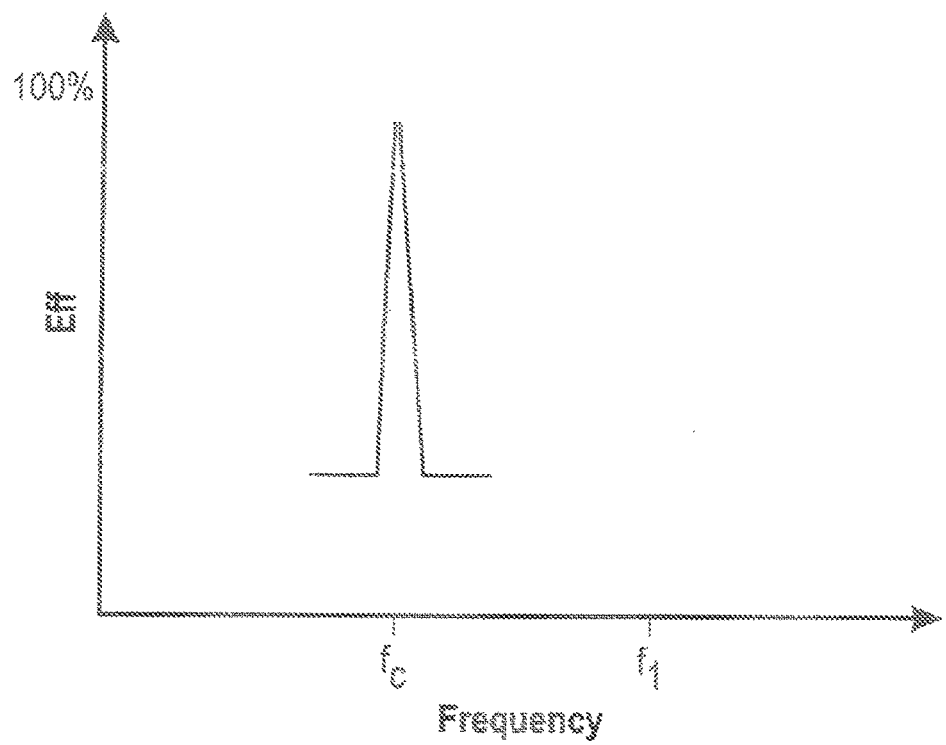
FIG. 2 is a graph illustrating ultrasound efficiency at a frequency, in accordance with various non-limiting embodiments.

Moving to FIG. 2, a graph illustrates efficiency of an ultrasound transducer at specific frequency $f_c$, in accordance with various embodiments. Efficiency of a transducer is defined as the ratio of the power output in the desired form to the total power input. Mathematically, if $P_{in}$ represents the total power input and $P_{out}$ represents the power output in the desired form, then the efficiency E, as a ratio between 0 and 1, is given by:

$$E = P_{out}/P_{in} \qquad \text{Equation 1}$$

If E % represents the efficiency as a percentage, then:

$$E\% = 100 P_{out}/P_{in} \qquad \text{Equation 2}$$

In general, a transducer is not 100% efficient and power is typically lost during the operation of the transducer in the form of heat. However, for a high-Q transducer, efficiency can approach 100% and heat generated by the transducer is minimized. A transducer is most efficient at specific frequency $f_c$, as illustrated in FIG. 2. The transducer has the maximum power output at frequency $f_c$.

Figure 3:
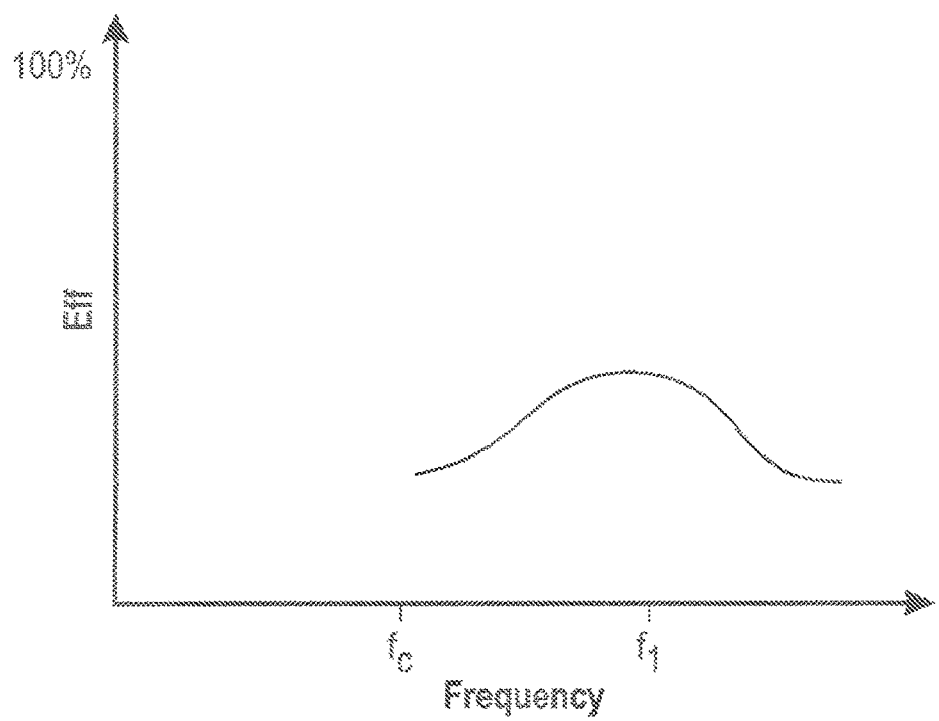
FIG. 3 is a graph illustrating ultrasound efficiency a frequency, in accordance with various non-limiting embodiments.

When a transducer operates, the transducer heats up over time and the temperature of the transducer changes. As the temperature of the transducer changes, the resonant frequency will shift towards frequency $f_t$, as illustrated in FIG. 3. This frequency shift decreases the efficiency of the transducer and, the power output from the transducer is significantly lower in the example of FIG. 3 as compared to the example of FIG. 2.

Transducer efficiency decreases due to changes in temperature of the transducer as a function of time. In addition, a change in temperature of the transducer will cause a frequency shift. The frequency shift changes as a function of increasing temperature of the transducer. A frequency shift decreases efficiency and can cause a system to change total power input to make up for a loss of power applied by the transducer. A frequency shift will change the impedance of the transducer.

In various embodiments, systems and methods, described herein, monitor transducer temperature and report changes in temperature to a controller to modify the frequency generation to the transducer. In various embodiments, systems and methods can monitor transducer temperature and report changes in temperature to a controller to modify the total power input to the transducer. In various embodiments, systems and methods can monitor efficiency and controls transducer temperature to prevent energy transmission from a shift in frequency.

In various embodiments, systems and methods can at least one of monitor transducer temperature and control transducer temperature. In various embodiments, systems and methods can operate the transducer to at or near maximum efficiency of power over a period of time. In various embodiments, systems and methods can operate the transducer to at or near maximum efficiency of power as a temperature of the transducer changes. In various embodiments, systems and methods can modify temperature of the transducer to maintain operation at or near maximum efficiency of power. In various embodiments, systems and methods can prevent a change in impedance of the transducer.

In some embodiments, energy emission, such as, an ultrasound emission, can be directed to targeted tissue to initiate a desired treatment to the targeted tissue. If the power of the energy emission, such as, an ultrasound emission, is too high, the targeted tissue can be permanently damaged, which provide pain to the patient being treated. In addition, if the power of the energy emission, such as, an ultrasound emission, is too high, the desired treatment to the targeted tissue may not be effective. If the power of the energy emission, such as, an ultrasound emission, is too low, the desired treatment to the targeted tissue may not be effective.

If the efficiency of the transducer degrades, the power of energy emission decreases. If the temperature of the transducer changes, the efficiency of the transducer changes and the power of energy emission decreases. For the most effective treatment to targeted tissue, power of energy emission is constant. Various embodiments provide methods and systems to provide constant energy emission from transducer 110 that is directed to targeted tissue.

Figure 4:
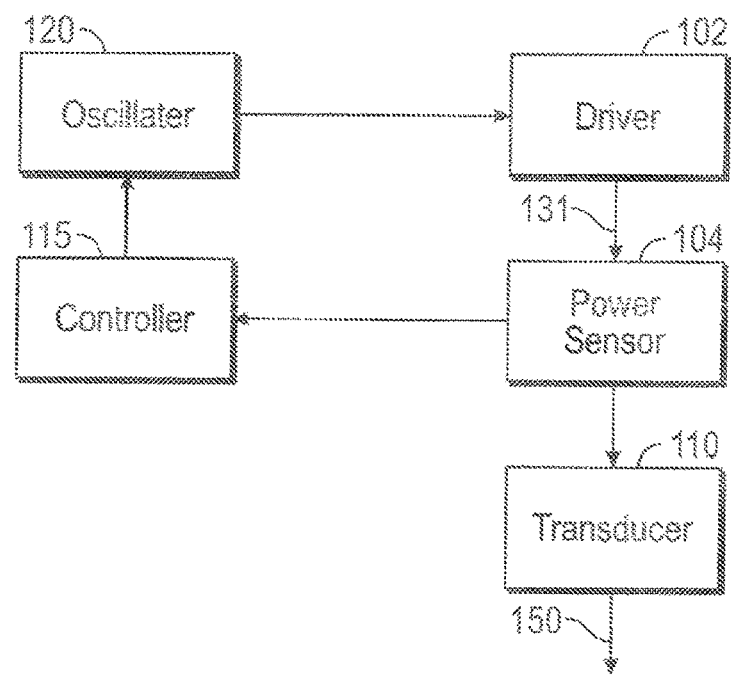
FIG. 4 is a block diagram illustrating a system in accordance with various non-limiting embodiments.

Referring to FIG. 4, system 131 is illustrated, in accordance with some embodiments. System 131 can comprise drivers 102, power sensor 104, transducer 110, controller 115, and oscillator 120. In various embodiments, oscillator 120 generates a frequency which is communicated to drivers 102 to power transducer 110 to produce energy transmission 150 at the frequency. Oscillator 120 can be an oscillator or any frequency generator, now known or later developed. For example, oscillator 120 can be but is not limited to, a function generator, a frequency generator, a waveform generator, a signal generator, pitch generator, a wave generator, or a pulse generator, frequency synthesizer, direct digital synthesizer, or combinations thereof. In some embodiments, oscillator 120 can be combined with or integrated to drivers 102. In some embodiments, oscillator 120 is programmable. In some embodiments, controller 115 can be combined with or integrated to at least one of oscillator 120 and drivers 102. In some embodiments, power sensor 104 can be combined with or integrated to at least one of oscillator 120, controller 115 and drivers 102. In some embodiments, power sensor 104 can be combined with or integrated to at least one of oscillator 120, and drivers 102. In some embodiments, power sensor 104 can be combined with or integrated to at least one of controller 115 and drivers 102. In some embodiments, power sensor 104 can be combined with or integrated to at least one of oscillator 120, and controller 115. In some embodiments, power sensor 104 can be combined with or integrated to drivers 102. In some embodiments, power sensor 104 can be combined with or integrated to oscillator 120. In some embodiments, power sensor 104 can be combined with or integrated to controller 115.

In some embodiments, power sensor 104 monitors power input from drivers 102 to transducer 110. In some embodiments, power sensor 104 communicates with controller 115, which controls oscillator 120. In some embodiments, controller 115 receives signal from power sensor 104 and controls a frequency generated by oscillator 120 based on the received signal. In some embodiments, power sensor 104 communicates a power level of the power input from drivers 102.

As transducer 110 efficiency of energy transmission 150 degrades, for example as illustrated in FIG. 3, drivers 102 changes the power input to transducer 110. In some embodiments, power sensor 104 detects the change in power input to transducer 110 and communicates with controller 115, which controls oscillator 120 to change in the power level of the power input from supply and/or drivers 102. In some embodiments, oscillator 120 generates a correction to the frequency which is communicated to the drivers 102, which is based on the communication from the power sensor 104. In some embodiments, the correction to the frequency lowers the power level of power input from drivers 102. In some embodiments, energy transmission 150 is corrected to specific frequency Q as illustrated in FIG. 2. If this correction to specific frequency f does not lower the power input from the drivers 102 to transducer 110 below a threshold, power sensor 104 communicates this elevated power level to controller 115, which controls oscillator 120 for another generation of a correction to the frequency. In some embodiments, system 131 comprises a shut off power function, which is initiated if power sensor 104 detects a power level that is above a predetermined threshold. In some embodiments, the shut off power function prevents the damaging or destroying of transducer 110.

In some embodiments, the thickness of the transduction element of transducer 110 may be configured to be uniform. That is, the transduction element may be configured to have a thickness that is generally substantially the same throughout. In another exemplary embodiment, the transduction element may also be configured with a variable thickness, and/or as a multiple damped device. For example, the transduction element of transducer 110 may be configured to have a first thickness selected to provide a specific operating frequency of a lower range, for example from approximately 1 kHz to 3 MHz. The transduction element may also be configured with a second thickness selected to provide a specific operating frequency of a higher range, for example from approximately 3 to 100 MHz or other frequency ranges described herein.

In yet another exemplary embodiment, transducer 110 may be configured as a single broadband transducer excited with two or more frequencies to provide an adequate output for raising the temperature within ROI 215 to the desired level. Transducer 110 may also be configured as two or more individual transducers, wherein each transducer 110 may comprise a transduction element. The thickness of the transduction elements may be configured to provide specific operating frequencies in a desired treatment range. For example, in some embodiments, transducer 110 may comprise a first transducer 110 configured with a first transduction element having a thickness corresponding to a specific frequency range of approximately 1 MHz to 3 MHz, and a second transducer 110 configured with a second transduction element having a thickness corresponding to a specific frequency of approximately 3 MHz to 100 MHz or frequency ranges described herein.

Moreover, in some embodiments, any variety of mechanical lenses or variable focus lenses, e.g. liquid-filled lenses, may also be used to focus and or defocus the energy field. For example, transducer 110 may also be configured with an electronic focusing array in combination with one or more transduction elements to facilitate changed flexibility in treating ROI 215. Array may be configured in a manner similar to transducer 110. That is, array may be configured as an array of electronic apertures that may be operated by a variety of phases via variable electronic time delays. Accordingly, the electronic apertures of array may be manipulated, driven, used, configured to produce and/or deliver energy in a manner corresponding to the phase variation caused by the electronic time delay. For example, these phase variations may be used to deliver defocused beams, planar beams, and/or focused beams, each of which may be used in combination to achieve different physiological effects in ROI 215.

Transduction elements may be configured to be concave, convex, and/or planar. For example, transduction elements can be configured to be concave in order to provide focused energy for treatment of ROI 215. In another exemplary embodiment, transduction elements may be configured to be substantially flat in order to provide substantially uniform energy to ROI 215. In addition, transduction elements may be configured to be any combination of concave, convex, and/or substantially flat structures. For example, a first transduction element may be configured to be concave, while a second transduction element may be configured to be substantially flat.

Moreover, transduction element can be any distance from the skin surface 204. In that regard, it can be far away from the skin surface 204 disposed within a long transducer 110 or it can be just a few millimeters from skin surface 204. In certain exemplary embodiments, positioning the transduction element closer to skin surface 204 is better for transmitting ultrasound at high frequencies. Moreover, both two and three dimensional arrays of transduction elements can be used in various embodiments.

In some embodiments, transducer 110 may also be configured as an annular array to provide planar, focused and/or defocused acoustical energy. For example, in some embodiments, an annular array may comprise a plurality of rings. Rings may be mechanically and electrically isolated into a set of individual elements, and may create planar, focused, or defocused waves. For example, such waves can be specified on-axis, such as by methods of adjusting corresponding phase delays. An electronic focus may be moved along various depth positions in ROI 215, and may enable variable strength or beam tightness, while an electronic defocus may have varying amounts of defocusing. In some embodiments, a lens and/or convex or concave shaped annular array may also be provided to aid focusing or defocusing such that any time differential delays can be reduced. Movement of annular array in one, two or three-dimensions, or along any path, such as through use of probes, motion mechanisms, any conventional robotic arm mechanisms, and the like may be implemented to scan and/or treat a volume or any corresponding space within ROI 215.

Figure 5:
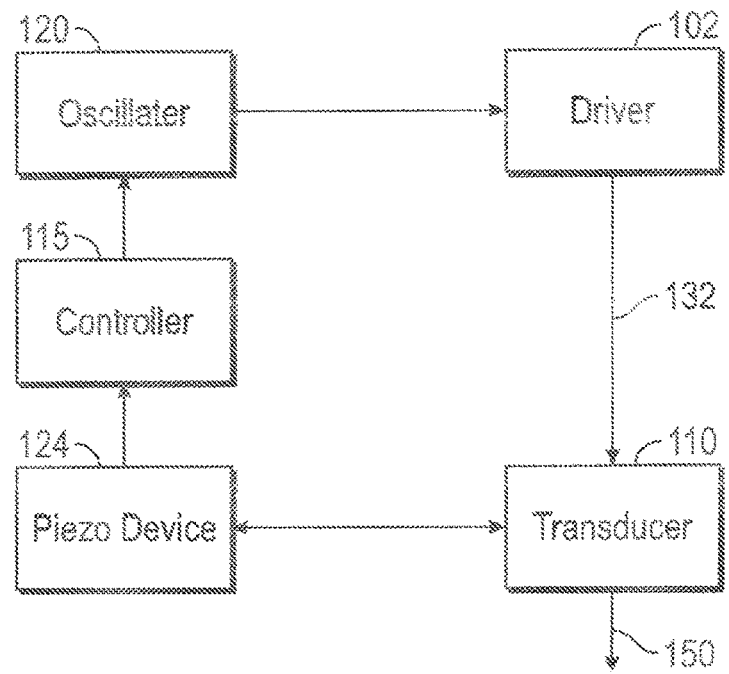
FIG. 5 is a block diagram illustrating a system in accordance with various non-limiting embodiments.

In FIG. 5, system 132 is illustrated, in accordance with some embodiments. System 132 can comprise drivers 102, transducer 110, piezoelectric sensor 124, controller 115, and oscillator 120. In some embodiments, piezoelectric sensor 124 can be combined with or integrated to at least one of oscillator 120 and drivers 102. In some embodiments, piezoelectric sensor 124 can be combined with or integrated into oscillator 120. In some embodiments, piezoelectric sensor 124 can be combined with into integrated to drivers 102. In various embodiments, oscillator 120 generates a frequency which is communicated to drivers 102 to power transducer 110 to produce energy transmission 150 at the frequency. In some embodiments, piezoelectric sensor 124 monitors heat generated by transducer 110. In some embodiments, piezoelectric sensor 124 is coupled to transducer 110. In some embodiments, piezoelectric sensor 124 is integrated to transducer 110. For example, piezoelectric sensor 124 may be a portion of transducer 110, which that is isolated or insulation from the rest of transducer 110, and may comprise identical materials as transducer 110. However, in one aspect of this example, piezoelectric sensor 124 has the opposite temperature coefficient of transducer (same coefficient but opposite sign) and the piezoelectric sensor 124 changes temperature at the same rate as transducer 110, thus compensating for changes in temperature of transducer 110.

Piezoelectric sensor 124 can comprise ceramic, or any other material or combination of material described herein. In some embodiments, piezoelectric sensor 124 is configured with a temperature coefficient that is lower than the temperature coefficient of transducer 110. In some embodiments, piezoelectric sensor 124 is configured with temperature coefficient, which is negative. In various embodiments, piezoelectric sensor 124 generates an electric potential in response to a temperature change, and communicates this electric potential to controller 115, which controls oscillator 120. In some embodiments, piezoelectric sensor 124 communicates with oscillator 120. In some embodiments, controller 115 receives signal from piezoelectric sensor 124 and controls a frequency generated by oscillator 120 based on the received signal. In some embodiments, piezoelectric sensor 124 communicates the heat generated by transducer 110, which can be communicated using temperature.

As transducer 110 efficiency of energy transmission 150 degrades, for example as illustrated in FIG. 3, heat generated by transducer 110 changes. For example, drivers 102 changes the power input to transducer 110, which can change the heat generated by transducer 110. In some embodiments, piezoelectric sensor 124 detects the change in heat generation by transducer 110 and communicates with controller 115, which controls oscillator 120, the change in heat generation. In some embodiments, oscillator 120 generates a correction to the frequency which is communicated to the drivers 102, which is based on the communication from the piezoelectric device 124. In some embodiments, the correction to the frequency lowers the power level of power input from drivers 102, which can lower the amount of heat that is generated by transducer 110. In some embodiments, the correction to the frequency lowers the power level of power input from drivers 102. In some embodiments, energy transmission 150 is corrected to specific frequency $f_c$ as illustrated in FIG. 2. If this correction to specific frequency $f_c$ does not lower the power input from the drivers 102 to transducer 110 below a threshold, piezoelectric sensor 124 communicates this elevated heat generation by transducer 110 to oscillator 124 for another generation of a correction to the frequency. In some embodiments, system 132 comprises a shut off power function, which is initiated if piezoelectric sensor 124 detects a heat generation level or a temperature of transducer 110 is above a predetermined threshold. In some embodiments, the shut off power function prevents the damaging or destroying of transducer 110.

Figure 6:
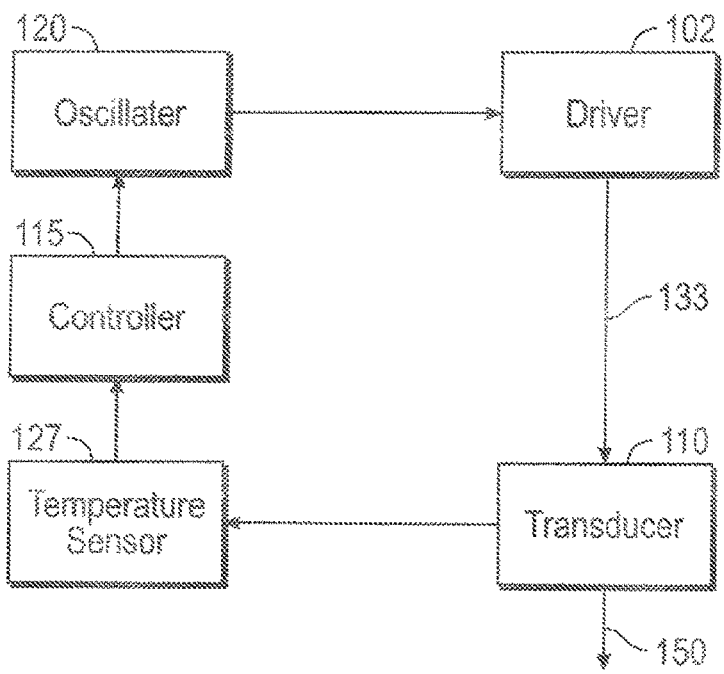
FIG. 6 is a block diagram illustrating a system in accordance with various non-limiting embodiments.

Turning to FIG. 6, system 133 is illustrated, in accordance with some embodiments. System 133 can comprise drivers 102, transducer 110, temperature sensor 127, and oscillator 120. In some embodiments, temperature sensor 127 can be combined with or integrated to at least one of oscillator 120 and drivers 102. In various embodiments, oscillator 120 generates a frequency which is communicated to drivers 102 to power transducer 110 to produce energy transmission 150 at the frequency. In some embodiments, temperature sensor 127 monitors temperature of transducer 110. In some embodiments, temperature sensor 127 coupled to transducer 110. In some embodiments, temperature sensor 127 is integrated to transducer 110. Temperature sensor 127 can be any suitable temperature sensor, now known or later developed. In some embodiments, temperature sensor 127 communicates with controller 115, which communicates with oscillator 120. In some embodiments, temperature sensor 127 communicates with oscillator 120. In some embodiments, controller 115 receives signal from temperature sensor 127 and controls a frequency generated by oscillator 120 based on the received signal. In some embodiments, temperature sensor 127 communicates the temperature of by transducer 110.

As transducer 110 efficiency of energy transmission 150 degrades, for example as illustrated in FIG. 3, heat generated by transducer 110 changes. For example, drivers 102 changes the power input to transducer 110, which can change the heat generated by transducer 110. In some embodiments, temperature sensor 127 detects the change in heat generation by transducer 110 and communicates with controller 115, which controls oscillator 120, the change in heat generation. In some embodiments, oscillator 120 generates a correction to the frequency which is communicated to the drivers 102, which is based on the communication from the piezoelectric device 124. In some embodiments, the correction to the frequency lowers the power level of power input from drivers 102, which can lower the amount of heat that is generated by transducer 110. In some embodiments, the correction to the frequency lowers the power level of power input from drivers 102. In some embodiments, energy transmission 150 is corrected to specific frequency $f_c$ as illustrated in FIG. 2. If this correction to specific frequency $f_c$ does not lower the power input from the drivers 102 to transducer 110 below a threshold, temperature sensor 127 communicates this elevated heat generation by transducer 110 to oscillator 124 for another generation of a correction to the frequency. In some embodiments, system 132 comprises a shut off power function, which is initiated if temperature sensor 127 detects a heat generation level or a temperature of transducer 110 is above a predetermined threshold. In some embodiments, the shut off power function prevents the damaging or destroying of transducer 110.

Figure 7:
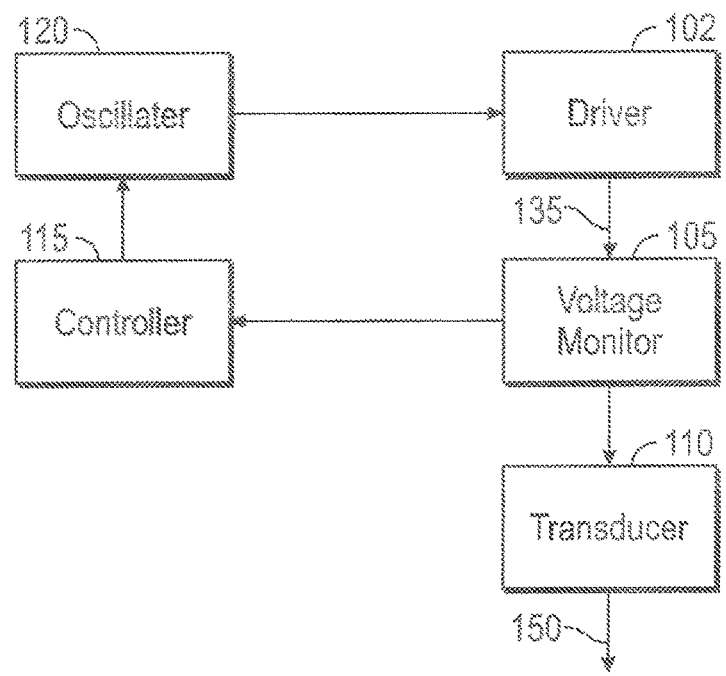
FIG. 7 is a block diagram illustrating a system in accordance with various non-limiting embodiments.

Moving to FIG. 7, system 135 is illustrated, in accordance with some embodiments. System 135 can comprise drivers 102, voltage monitor 105, transducer 110, controller 115, and oscillator 120. In various embodiments, oscillator 120 generates a frequency which is communicated to drivers 102 to power transducer 110 to produce energy transmission 150 at the frequency. Oscillator 120 can be an oscillator or any frequency generator, now known or later developed. For example, oscillator 120 can be but is not limited to, a function generator, a frequency generator, a waveform generator, a signal generator, pitch generator, a wave generator, or a pulse generator, frequency synthesizer, direct digital synthesizer, or combinations thereof. In some embodiments, oscillator 120 can be combined with or integrated to drivers 102. In some embodiments, oscillator 120 is programmable. In some embodiments, controller 115 can be combined with or integrated to at least one of oscillator 120 and drivers 102. In some embodiments, voltage monitor 105 can be combined with or integrated to at least one of oscillator 120, controller 115 and drivers 102. In some embodiments, voltage monitor 105 can be combined with or integrated to at least one of oscillator 120, and drivers 102. In some embodiments, voltage monitor 105 can be combined with or integrated to at least one of controller 115 and drivers 102. In some embodiments, voltage monitor 105 can be combined with or integrated to at least one of oscillator 120, and controller 115. In some embodiments, voltage monitor 105 can be combined with or integrated to drivers 102. In some embodiments, voltage monitor 105 can be combined with or integrated to oscillator 120. In some embodiments, voltage monitor 105 can be combined with or integrated to controller 115. In some embodiments, voltage monitor 105 monitors voltage of power from drivers 102 to transducer 110. In some embodiments, voltage monitor 105 communicates with controller 115, which controls oscillator 120. In some embodiments, controller 115 receives signal from voltage monitor 105 and controls a frequency generated by oscillator 120 based on the received signal. In some embodiments, voltage monitor 105 communicates a voltage level of the voltage of power from drivers 102.

As transducer 110 efficiency of energy transmission 150 degrades, for example as illustrated in FIG. 3, drivers 102 changes the voltage of power to transducer 110. In some embodiments, voltage monitor 105 detects the increase in voltage of power to transducer 110 and communicates with controller 115, which controls oscillator 120 to change in the voltage level of the voltage of power from supply and/or drivers 102. In some embodiments, oscillator 120 generates a correction to the frequency which is communicated to the drivers 102, which is based on the communication from the voltage monitor 105. In some embodiments, the correction to the frequency lowers the voltage level of voltage of power from drivers 102. In some embodiments, energy transmission 150 is corrected to specific frequency fc as illustrated in FIG. 2. If this correction to specific frequency fc does not lower the voltage of power from the drivers 102 to transducer 110 below a threshold, voltage monitor 105 communicates this elevated voltage level to controller 115, which controls oscillator 120 for another generation of a correction to the frequency. In some embodiments, system 135 comprises a shut off power function, which is initiated if voltage monitor 105 detects a voltage level that is above a predetermined threshold. In some embodiments, the shut off power function prevents the damaging or destroying of transducer 110.

Figure 8:
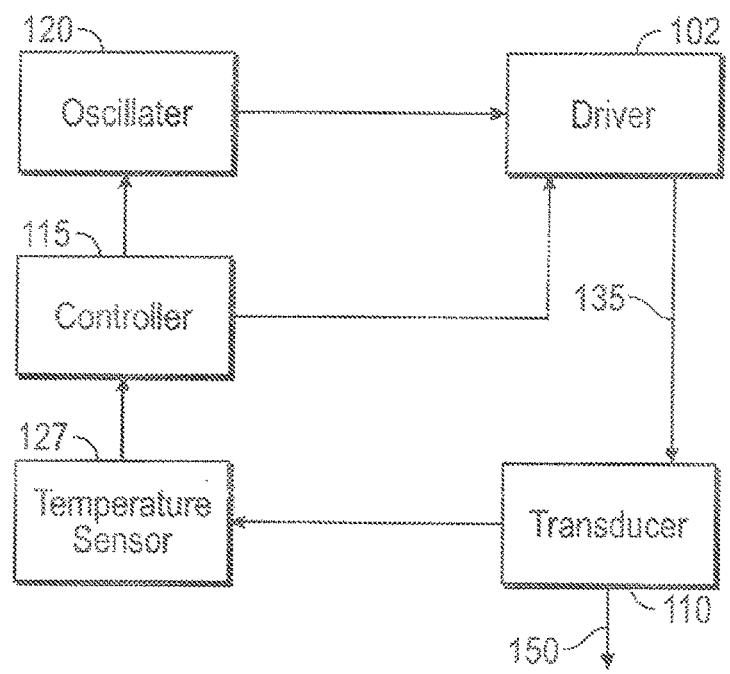
FIG. 8 is a block diagram illustrating a system in accordance with various non-limiting embodiments.

FIG. 8 With reference to FIG. 8, system 135 is illustrated, in accordance with some embodiments. System 135 can comprise drivers 102, transducer 110, temperature sensor 127, and oscillator 120. In some embodiments, temperature sensor 127 can be combined with or integrated to at least one of oscillator 120 and drivers 102. In various embodiments, oscillator 120 generates a frequency which is communicated to drivers 102 to power transducer 110 to produce energy transmission 150 at the frequency. In some embodiments, temperature sensor 127 monitors temperature of transducer 110. In some embodiments, temperature sensor 127 coupled to transducer 110. In some embodiments, temperature sensor 127 is integrated to transducer 110. Temperature sensor 127 can be any suitable temperature sensor, now known or later developed. In some embodiments, temperature sensor 127 communicates with controller 115, which communicates with oscillator 120. In some embodiments, temperature sensor 127 communicates with oscillator 120. In some embodiments, controller 115 receives signal from temperature sensor 127 and controls a frequency generated by oscillator 120 based on the received signal. In some embodiments, temperature sensor 127 communicates the temperature of by transducer 110. As transducer 110 efficiency of energy transmission 150 degrades, for example as illustrated in FIG. 3, drivers 102 changes the power to transducer 110, which change the voltage across the transducer 110. In some embodiments, controller 115 detects the change in voltage across transducer 110 and communicates with controller 115. In some embodiments, oscillator 120 generates a correction to the frequency which is communicated to the drivers 102, which is based on the communication from controller 115. In some embodiments, the correction to the frequency lowers the voltage level of voltage across transducer 110. In some embodiments, energy transmission 150 is corrected to specific frequency fc as illustrated in FIG. 2. If this correction to specific frequency fc does not lower the voltage across transducer 110 below a threshold, controller 115 communicates this elevated voltage level to oscillator 120 for another generation of a correction to the frequency.

As transducer 110 efficiency of energy transmission 150 degrades, for example as illustrated in FIG. 3, heat generated by transducer 110 changes. For example, drivers 102 changes the power input to transducer 110, which can change the heat generated by transducer 110. In some embodiments, temperature sensor 127 detects the change in heat generation by transducer 110 and communicates with controller 115, which controls oscillator 120, the change in heat generation. In some embodiments, oscillator 120 generates a correction to the frequency which is communicated to the drivers 102, which is based on the communication from the piezoelectric device 124. In some embodiments, the correction to the frequency lowers the power level of power input from drivers 102, which can lower the amount of heat that is generated by transducer 110. In some embodiments, the correction to the frequency lowers the power level of power input from drivers 102. In some embodiments, energy transmission 150 is corrected to specific frequency fc as illustrated in FIG. 2. If this correction to specific frequency fc does not lower the power input from the drivers 102 to transducer 110 below a threshold, temperature sensor 127 communicates this elevated heat generation by transducer 110 to oscillator 124 for another generation of a correction to the frequency. In some embodiments, system 132 comprises a shut off power function, which is initiated if temperature sensor 127 detects a heat generation level or a temperature of transducer 110 is above a predetermined threshold. In some embodiments, the shut off power function prevents the damaging or destroying of transducer 110.

Various embodiments provide a method of sensing coupling of an ultrasound source to a target. In some embodiments, the method comprises providing an ultrasound sound source comprising a transducer, an acoustically transparent standoff, an acoustic window at a bottom surface of the standoff, and a frequency sweep function coupled to the transducer. In some embodiments, the method can comprise emitting ultrasound energy from the transducer; receiving reflected energy; frequency sweeping the transducer; determining the feedback from the frequency sweep is above a threshold level; and determining of the source is coupled to the target.

In some embodiments, if the feedback from the frequency is above the threshold level, then the source is not coupled to the target. In some embodiments, if the feedback from the frequency is below the threshold level, then the source is coupled to the target.

In some embodiments, the window is a half wavelength thick. In some embodiments, the method can further comprise providing constant average output power from the source. In some embodiments, the method can further comprise terminating power to the source. In some embodiments, the sweep frequency has a period, which is calculated using a path length of the standoff and the speed of sound. In some embodiments, the method can further comprise comprising providing ultrasound energy to a target.

Various embodiments provide a system for determining whether an ultrasound source is coupled to a target. In some embodiments, the system comprises an ultrasound source comprising a transducer; an acoustically transparent standoff coupled to the transducer; a half wavelength acoustic window at a bottom surface of the standoff, and a frequency sweep function coupled to the transducer.

In some embodiments, the half wavelength acoustic window is a reflector when the ultrasound source is not coupled to the target.

In some embodiments, the half wavelength acoustic window is transparent to ultrasound energy when the ultrasound source is coupled to the target. In some embodiments, the system can further comprise a power to transducer termination function in communication with the frequency sweep function.

In some embodiments, the frequency sweep function provides a constant average output power from the ultrasound source when the ultrasound source is coupled to the target. In some embodiments, the system can further comprise a lens coupled to the ultrasound source.

Various embodiments provide a system for providing a constant average output of power from an ultrasound source. In some embodiments, the system comprises an ultrasound transducer coupled to a power supply; a controller in communication with the power supply; a chirp function in communication with and operable to monitor the ultrasound transducer; a feedback loop from the chirp function to the controller. In some embodiments, the controller is operable to change a parameter on the transducer based on the feedback to provide a constant average output of power from the ultrasound transducer.

In some embodiments, the system can further comprise a coupling device in acoustic communication with the ultrasound transducer. In some embodiments, the system can further comprise a half wavelength acoustic window in acoustic communication with the ultrasound transducer.

In some embodiments the coupling device contains a medium configured to be transparent to ultrasound energy. In some embodiments, the system can further comprise a contact sensor operable to determine if the ultrasound transducer is coupled to a target. In some embodiments, the controller is operable to control the power supply to change an amount of power provided to the ultrasound transducer.

In various embodiments, ultrasound probe 205 can comprise a tissue contact sensor. In some embodiments, tissue contact sensor communicates whether ultrasound probe 205 is coupled to the ROI 215. The tissue contact sensor may measure a capacity of a skin surface 204 above the ROI 215 and communicate a difference between the capacitance of the contact to the skin surface 204 and the capacitance of air. In some embodiments, the tissue contact sensor is initiated or turned on by pressing ultrasound probe against skin surface 204.

Figure 9:
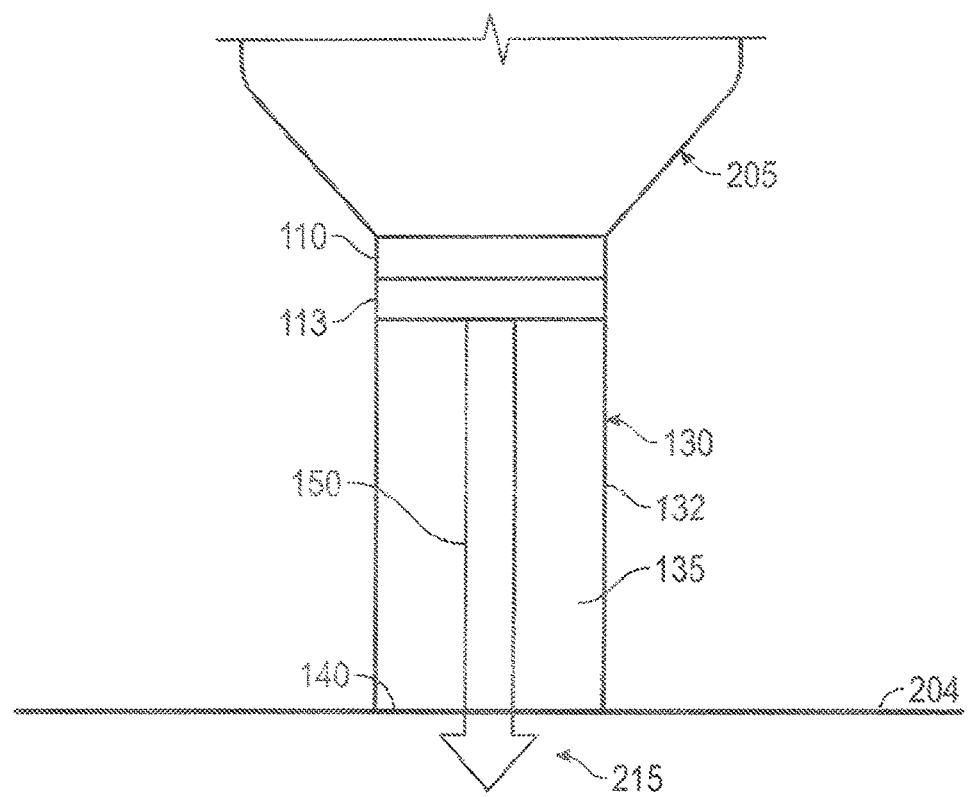
FIG. 9 is a diagram illustrating a transducer system coupled to tissue in accordance to various non-limiting examples.
Figure 10:
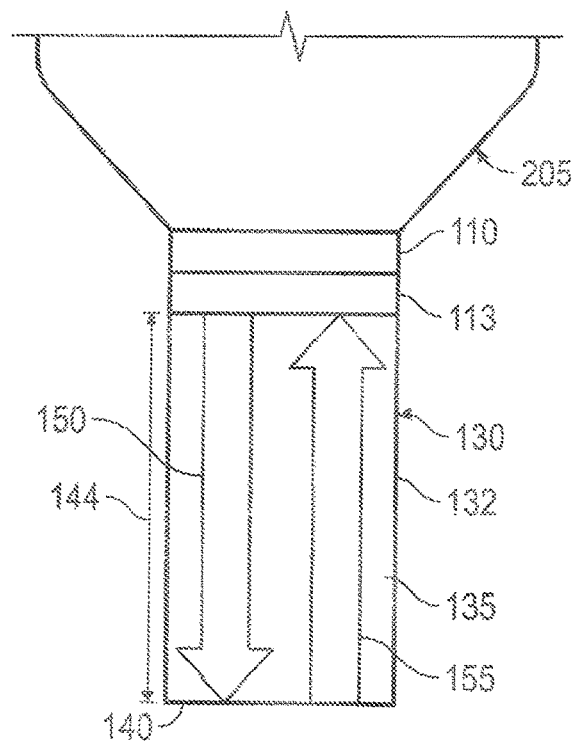
FIG. 10 is a diagram illustrating a transducer system not coupled to tissue in accordance to various non-limiting examples.

In various embodiments, as illustrated in FIGS. 9 and 10, a coupling device having a coupling sensor system is illustrated. Coupling device 130 comprises enclosure 132 which can be filled with coupling medium 135. Coupling device 130 further comprises a window 140 which is essentially transparent to ultrasound energy. In some embodiments, coupling device 130 comprises transducer 110. In some embodiments, coupling device 130 may comprise matching layer and/or lens 113. Coupling device 130 is part of or connects to probe 205. In some embodiments, transducer 110 is separate from the coupling device 130. In some embodiments, transducer 110 and matching layer and/or lens 113 are separate from coupling device 130. Coupling device 130 comprises path length 144, which is the distance from transducer 110 to window 140.

In some embodiments, coupling device 130 is configured to provide ultrasound energy 150 to ROI 215. In some embodiments, coupling device 130 is configured to provide focused ultrasound energy 150 to ROI 215. In some embodiments, coupling device 130 is configured to provide unfocused ultrasound energy 150 to ROI 215. In some embodiments, coupling device 130 is configured to provide defocused ultrasound energy 150 to ROI 215.

In some embodiments, window 140 is a half wavelength ("$\lambda$") thick. In some embodiments, window 140 is a multiple of a half wave length thick, such as, for example. 1.5 wavelength thick. Window 140 can comprise any number of materials that are temperature stable within up to about 150° C. (for example plastics and polymers) or to higher temperatures (for example metals and alloys) and are able to be configured into ultrasound transmissive window having a multiple of a half wave length thick. In some embodiments, window 140 can be configured using a cross linked polystyrene material or a PE imide material.

In some embodiments, enclosure 132 is essentially impermeable to water. Enclosure 132 contains medium 135, which can be water or saline solution or other water based solution, a gel, or a solid. Medium 135 is essentially transparent to acoustic energy. In some embodiments, medium 135 has acoustic impedance very similar to or the same as tissue in the ROI 215. In some embodiments, medium 135 has acoustic impedance very similar to or the same as skin surface.

In some embodiments, ultrasound energy 150 is a continuous wave emission. As illustrated in FIG. 9, coupling device 130 couples transducer 110 to ROI 205 and facilitates the transfer of ultrasound energy 150 from transducer 110 through medium 135 and window 140 and into ROI 215. However, as illustrated in FIG. 10, if coupling device is uncoupled from ROI 205 and is coupled to air, window 140 becomes a reflector and reflects all or at least a majority of ultrasound energy 150 back to transducer as reflected energy 155.

In some embodiments, a DDS synthesizer and be coupler to transducer 110 and configured to frequency sweep transducer 110. In some embodiments, frequency sweep can monitor the constant average output power of transducer 110. In some embodiments, frequency sweep can be a step function of a set of different frequencies. In some embodiments, the frequency sweep is a chirp function. In some embodiments, the step function of a set of different frequencies can comprise a plurality of different frequencies. In some embodiments, the period of each sweep is 50 kHz. This sweep period is calculated using path length 144 equal to 15 mm and a time of flight of 20 microseconds. In some embodiments, the period of each sweep is 23 kHz. This sweep period is calculated using path length 144 equal to 32.6 mm and a time of flight of 43.5 microseconds. Using path length 144 and the time of flight of the ultrasound energy 150, an appropriate sweep period can be calculated for most configurations of coupling device 130.

Figure 11:
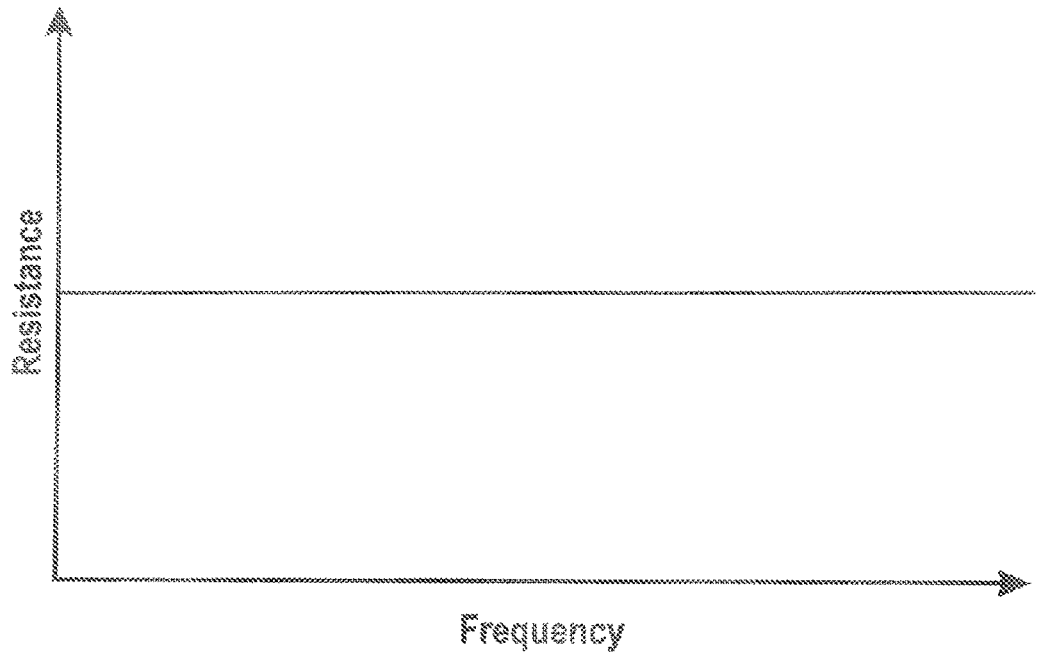
FIG. 11 is a graph illustrating resistance over time for a transducer system coupled to tissue in accordance with various non-limiting embodiments.
Figure 12:
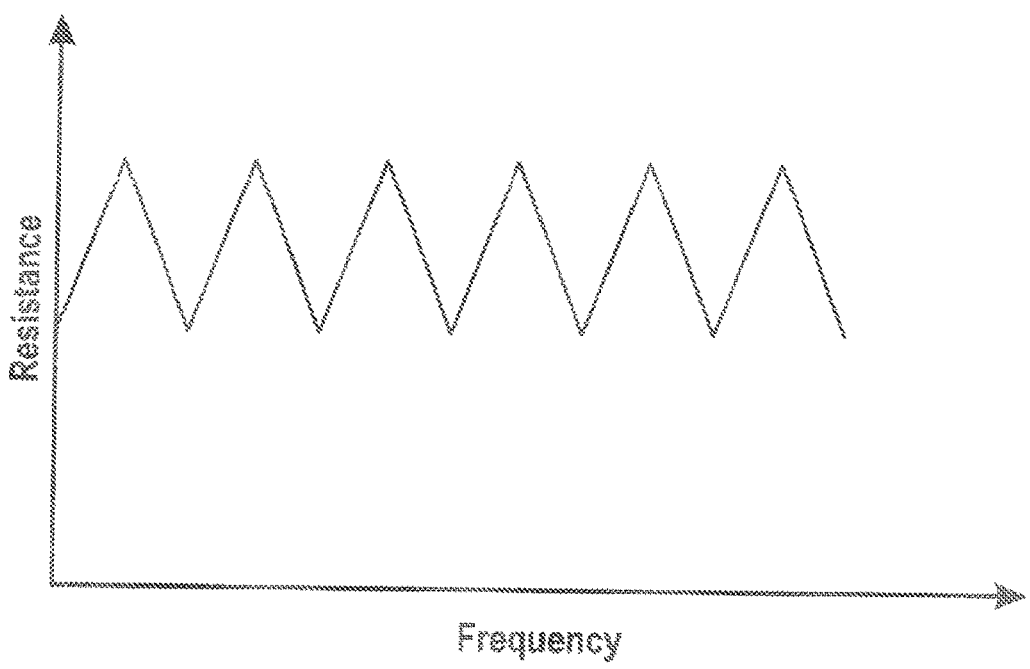
FIG. 12 is a graph illustrating resistance over time for a transducer system not coupled to tissue in accordance with various non-limiting embodiments.

In some embodiments, an output from the frequency sweep can be monitored as illustrated in FIGS. 11 and 12. The units for axis of the graphs in FIGS. 11 and 12 are resistance in the y axis and frequency in the x axis. FIG. 11 illustrates the feedback from a frequency sweep when coupling device 130 is coupled to ROI 215 as illustrated in FIG. 9. FIG. 12 illustrates the feedback from a frequency sweep when coupling device 130 is uncoupled (or coupled to air) as illustrated in FIG. 10. This difference in feedback from the frequency sweep can be a contact sensor. If the frequency sweep reports feedback is similar to FIG. 11, probe 205 continues to function providing ultrasound energy 150 to ROI 215. If the frequency sweep reports feedback is similar to FIG. 12, probe 205 is shut down as a safety mechanism and/or to protect the transducer from being damaged or destroyed.

In some embodiments, frequency sweep can monitor and adjust output power to achieve a constant average output power, even with variations in the medium 135 temperature and/or transducer 110 temperature. In various embodiments, contact sensor system can be combined with one or more different sensing techniques. For example, contact sensor can be combined with a hall detector. For example, contact sensor can be combined with an optical detector. For example, contact sensor can be combined with a conductive detector. For example, contact sensor can be combined with a piezo electric detector. For example, contact sensor can be combined with a mechanical detector. For example, contact sensor can be combined with a magnetic detector. In various embodiments, contact sensor system can be combined with at least one of a hall detector, optical detector, an acoustic impedance detector, a conductive detector, a piezo electric detector, a mechanical detector, a magnetic detector, an acoustic impedance detector, and combinations thereof.

In some embodiments, coupling device 130 can comprise a temperature sensor. In some embodiments, coupling device 130 can comprise two temperature sensors. For example, one of the temperature sensors can be in contact with medium 135 and the second temperature sensor can be in contact with transducer 110. In some embodiments, if the temperature as reported by a temperature is above 43° C., probes 205 stop emission of ultrasound energy 150.

The following patents and patent applications are incorporated by reference: US Patent Application Publication No. 20050256406, entitled "Method and System for Controlled Scanning, Imaging, and/or Therapy" published Nov. 17, 2005; US Patent Application Publication No. 20060058664, entitled "System and Method for Variable Depth Ultrasound Treatment" published Mar. 16, 2006; US Patent Application Publication No. 20060084891, entitled Method and System for Ultra-High Frequency Ultrasound Treatment" published Apr. 20, 2006; U.S. Pat. No. 7,530,958, entitled "Method and System for Combined Ultrasound Treatment" issued May 12, 2009; US Patent Application Publication No. 2008071255, entitled "Method and System for Treating Muscle, Tendon, Ligament, and Cartilage Tissue" published Mar. 20, 2008; U.S. Pat. No. 6,623,430, entitled "Method and Apparatus for Safely Delivering Medicants to a Region of Tissue Using Imaging, Therapy, and Temperature Monitoring Ultrasonic System, issued Sep. 23, 2003; U.S. Pat. No. 7,571,336, entitled "Method and System for Enhancing Safety with Medical Peripheral Device by Monitoring if Host Computer is AC Powered" issued Aug. 4, 2009; US Patent Application Publication No. 20080281255, entitled "Methods and Systems for Modulating Medicants Using Acoustic Energy" published Nov. 13, 2008; US Patent Application Publication No. 20060116671, entitled "Method and System for Controlled Thermal Injury of Human Superficial Tissue," published Jun. 1, 2006; US Patent Application Publication No. 20060111744, entitled "Method and System for Treatment of Sweat Glands," published May 25, 2006; US Patent Application Publication No. 20080294073, entitled "Method and System for Non-Ablative Acne Treatment and Prevention," published Oct. 8, 2009; U.S. Pat. No. 8,133,180, entitled "Method and System for Treating Cellulite," issued Mar. 13, 2012; U.S. Pat. No. 8,066,641, entitled "Method and System for Photoaged Tissue," issued Nov. 29, 2011; U.S. Pat. No. 7,491,171, entitled "Method and System for Treating Acne and Sebaceous Glands," issued Feb. 17, 2009; U.S. Pat. No. 7,615,016, entitled "Method and System for Treating Stretch Marks," issued Nov. 10, 2009; and U.S. Pat. No. 7,530,356, entitled "Method and System for Noninvasive Mastopexy," issued May 12, 2009.

It is believed that the disclosure set forth above encompasses at least one distinct invention with independent utility. While the invention has been disclosed herein, the specific embodiments thereof as disclosed and illustrated herein are not to be considered in a limiting sense as numerous variations are possible. The subject matter of the inventions includes all novel and non-obvious combinations and sub combinations of the various elements, features, functions and/or properties disclosed herein.

Various embodiments and the examples described herein are not intended to be limiting in describing the full scope of systems and methods of this invention. Equivalent changes, modifications and variations of various embodiments, materials, systems, and methods may be made within the scope of the present invention, with substantially similar results.

The invention claimed is:

1. A system comprising:
    an ultrasound source comprising a transducer;
    an acoustically transparent standoff acoustically coupled to the transducer;
    an acoustic window at a surface of the standoff, the acoustic window having a thickness of an integer multiple of half wavelength of ultrasound energy emitted by the ultrasound source; and
    an ultrasound controller coupled to the transducer, the ultrasound controller configured to cause the transducer to emit the ultrasound energy, the ultrasound energy being frequency swept over time, the ultrasound controller monitoring a coupling status of the ultrasound source by measuring at least a portion of the ultrasound energy that is reflected by the acoustic window.

* * * * *